US008282944B2

(12) United States Patent
Youngs et al.

(10) Patent No.: US 8,282,944 B2
(45) Date of Patent: Oct. 9, 2012

(54) METAL COMPLEXES INCORPORATED WITHIN BIODEGRADABLE NANOPARTICLES AND THEIR USE

(75) Inventors: Wiley J. Youngs, Akron, OH (US); Khadijah Hindi, Akron, OH (US); Doug Medvetz, Elyria, OH (US)

(73) Assignee: The University of Akron, Akron, OH (US)

( * ) Notice: Subject to any disclaimer, the term of this patent is extended or adjusted under 35 U.S.C. 154(b) by 239 days.

(21) Appl. No.: 12/601,591

(22) PCT Filed: May 29, 2008

(86) PCT No.: PCT/US2008/065026
§ 371 (c)(1),
(2), (4) Date: Apr. 6, 2010

(87) PCT Pub. No.: WO2008/150830
PCT Pub. Date: Dec. 11, 2008

(65) Prior Publication Data
US 2010/0204193 A1    Aug. 12, 2010

Related U.S. Application Data

(60) Provisional application No. 60/941,090, filed on May 31, 2007.

(51) Int. Cl.
*A61K 9/00* (2006.01)
*A61K 38/00* (2006.01)

(52) U.S. Cl. .................... 424/400; 977/911
(58) Field of Classification Search .................... 424/400
See application file for complete search history.

(56) References Cited

U.S. PATENT DOCUMENTS

| | | | |
|---|---|---|---|
| 3,930,867 A | 1/1976 | Bigelow | |
| 5,132,231 A | 7/1992 | Youngs et al. | |
| 5,262,532 A | 11/1993 | Tweedle et al. | |
| 5,405,957 A | 4/1995 | Tang et al. | |
| 6,025,496 A | 2/2000 | Herrmann et al. | |
| 6,288,197 B1 | 9/2001 | Youngs et al. | |
| 6,794,327 B2 | 9/2004 | Youngs et al. | |
| 6,919,448 B2 | 7/2005 | Youngs et al. | |
| 2004/0247690 A1 | 12/2004 | Yang | |
| 2006/0154911 A1 | 7/2006 | Batarseh | |
| 2007/0003603 A1 | 1/2007 | Karandikar et al. | |
| 2007/0021401 A1 | 1/2007 | Youngs et al. | |
| 2008/0267867 A1 | 10/2008 | Youngs et al. | |

FOREIGN PATENT DOCUMENTS

| | | |
|---|---|---|
| CN | 1926141 | 3/2007 |
| DE | 10342258 | 4/2005 |
| EP | 1660444 | 5/2006 |
| WO | 0238566 | 5/2002 |
| WO | 2005023760 | 3/2005 |
| WO | 2005111619 | 11/2005 |

OTHER PUBLICATIONS

Barrow, D. J. et al., "Thermodynamic Studies of Cationic Metalloporphyrins Binding to DNA Via Isothermal Titration Calorimetry", Mar. 2006, Abstracts of Papers, 231st ACS National Meeting, pp. 26-30, Atlanta, GA, United States.
Panyam, J. et al., "Biodegradable nanoparticles for drug and gene delivery to cells and tissue", Adv. Drug Delivery Rev., 2003, pp. 329-47, vol. 55, University of Nebraska Medical Center, Omaha, NE.
Liang, H. et al., "Paclitaxel-Loaded Poly(glutamic acid)-poly(lactide) Nanoparticles as a Targeted Drug Delivery System against Cultured HepG2 Cells", Bioconjugate Chem., 2006, p. 291-299, vol. 17, Published on web Feb. 18, 2006.
Andianov, A. et al., "Degradation of Polyaminophosphazenes: Effects of Hydrolytic Environment and Polymer Processing", Biomacromolecules., 2006, pp. 1581-1586, vol. 7, Published on web Apr. 11, 2006.
Aysegul, K. et al., "Synthesis from Caffeine of a Mixed N-Heterocyclic Carbene-Silver Acetate Complex Active against Resistant Respiratory Pathogens", J. Med. Chem., 2006, pp. 6811-6818, vol. 49, Published on web Oct. 20, 2006.
Korean Intellectual Property Office, PCT International Search Report for International Application No. PCT/US08/065026, Dec. 12, 2008, 12 pages.
Korean Intellectual Property Office, PCT International Search Report for International Application No. PCT/US08/070697, Feb. 11, 2009, 13 pages.
Anthony J. Arduengo et al., Electronic Stabilization of Nucleophilic Carbenes, Journal of the American Chemical Society, Jul. 1, 1992, pp. 5530-5534, vol. 114, No. 4, American Chemical Society, New York, N.Y. U.S.A.
J. C. Garrison et al., Synthesis and structural characterization of a silver complex of a mixed-donor N-heterocyclic carbene linked cyclophane, Chemical Communications—CHEMCOM, The Royal Society of Chemistry 2001, Great Britain, Aug. 21, 2001, pp. 1780-1781, vol. 2001, No. 18, Department of Chemistry, University of Akron, Akron OH, First published as an Advance Article on the web Aug. 21, 2001.

*Primary Examiner* — David J Blanchard
*Assistant Examiner* — Devang Thakor
(74) *Attorney, Agent, or Firm* — Renner Kenner Greive Bobak Taylor & Weber (57) ABSTRACT

The invention is directed to providing a compound for treating cancer, the compound comprising a metal complex having predetermined characteristics, and which may be incorporated into a polymeric nanoparticle or other delivery system for delivering the metal complex for action on tumor cells. The metal complex for treating cancer wherein the metal complex is a silver(I) salt, a silver(I) macrocyclic metal complex, a silver(I) N-heterocyclic carbene or mixtures thereof. The invention is also directed to a silver(I) macrocyclic metal complex and a silver(I) N-heterocyclic carbine, and methods of treating cancerous cells in a mammal including the steps of administering an effective amount of a silver(I) metal salt, such as by incorporating the material into a biodegradable polymeric nanoparticle.

5 Claims, 7 Drawing Sheets

FIG. 1

| | 0.5 μm | 1.0 μm | 2.5 μm | 5.0 μm | 10 μm | 15 μm | 20 μm | 25 μm |
|---|---|---|---|---|---|---|---|---|
| Percent control growth | | | | | | | | |
| Cisplatin | 103.1474355 | 94.23927402 | 48.9403251 | 15.3408765 | 5.289759 | 1.447361 | -0.76963 | 0.11487 |
| Carboplatin | 101.9512745 | 101.0940672 | 99.221746 | 90.7229867 | 62.82991 | 40.73427 | 25.84029 | 15.19851 |
| Formula 22 | 99.568623 | 96.29923941 | 94.1593824 | 83.630378 | 69.37223 | 57.81587 | 50.48814 | 34.40799 |
| Percent SEM | | | | | | | | |
| Cisplatin | 0.6638807813 | 0.7355774355 | 1.19100449 | 0.82715451 | 0.487178 | 0.314097 | 0.380132 | 0.617522 |
| Carboplatin | 0.8951162584 | 1.33596824 | 1.70832834 | 1.34343102 | 1.803796 | 0.924567 | 0.426047 | 0.444752 |
| Formula 22 | 2.397262571 | 3.06514246 | 3.07600415 | 5.45477353 | 2.994538 | 3.883971 | 3.451773 | 2.732056 |

| Percent control growth | 0.5 μm | 1.0 μm | 2.5 μm | 5.0 μm | 10 μm | 15 μm | 20 μm | 25 μm |
|---|---|---|---|---|---|---|---|---|
| Cisplatin | 105.812897 | 95.2316076 | 59.17348 | 23.22888 | 8.787466 | 1.827884 | -2.90645 | -4.67757 |
| Carboplatin | 106.973555 | 104.720862 | 95.73947 | 87.99216 | 73.17336 | 51.43976 | 30.28404 | 24.36827 |
| Formula 22 | 100.785498 | 101.752266 | 98.48943 | 82.59269 | 67.28921 | 61.92804 | 44.58116 | 14.25982 |

| Percent SEM | | | | | | | | |
|---|---|---|---|---|---|---|---|---|
| Cisplatin | 2.8137773 | 2.52738158 | 1.266435 | 0.970976 | 1.748769 | 0.925447 | 0.419656 | 0.289136 |
| Carboplatin | 3.10557816 | 2.34838519 | 2.000971 | 3.257769 | 1.890072 | 3.051151 | 3.654746 | 0.660352 |
| Formula 22 | 2.54793844 | 1.40493135 | 2.341107 | 2.482293 | 6.779945 | 8.706919 | 9.358017 | 4.286348 |

| Percent control growth | 0.5 μm | 1.0 μm | 2.5 μm | 5.0 μm | 10 μm | 15 μm | 20 μm | 25 μm |
|---|---|---|---|---|---|---|---|---|
| Cisplatin | 90.1442164 | 48.6565735 | 7.498055 | 0.664233 | -1.45413 | -1.95679 | -1.92089 | -2.05254 |
| Carboplatin | 103.221845 | 91.989241 | 82.92013 | 55.06374 | 28.42942 | 20.72272 | 4.829844 | 3.192609 |
| SCC5 | 92.3974858 | 92.6908111 | 83.99282 | 53.40916 | 22.44238 | 15.28884 | 6.614786 | -0.67046 |

| Percent SEM | | | | | | | | |
|---|---|---|---|---|---|---|---|---|
| Cisplatin | 0.97329744 | 1.42692986 | 0.411909 | 0.14043 | 0.130459 | 0.104115 | 0.160043 | 0.161444 |
| Carboplatin | 1.474480903 | 2.7233931 | 3.206863 | 1.147919 | 10.93877 | 12.3482 | 0.473345 | 0.266383 |
| SCC5 | 2.723103382 | 3.21260958 | 3.773369 | 7.792451 | 5.609132 | 4.265511 | 1.706976 | 0.612203 |

METAL COMPLEXES INCORPORATED WITHIN BIODEGRADABLE NANOPARTICLES AND THEIR USE

TECHNICAL FIELD

The invention relates to metal complexes which may be used in treating cancer. In an example, the invention relates to silver metal complexes that are incorporated within biodegradable materials, such as nanoparticles, and are used in treating cancer.

BACKGROUND OF THE INVENTION

Silver has long been used for its antimicrobial properties. This usage predates the scientific or medical understanding of its mechanism. For example, the ancient Greeks and Romans used silver coins to maintain the purity of water. Today silver is still used for this same purpose by NASA on its space shuttles. Treatment of a variety of medical conditions using silver nitrate was implemented before 1800. A 1% silver nitrate solution is still widely used today after delivery in infants to prevent gonorrheal ophthalmia. Since at least the later part of the nineteenth century, silver has been applied in a variety of different forms to treat and prevent numerous types of bacteria related afflictions.

Other treatments, such as the application of silver foil to post surgical wounds to prevent infection survived as a medical practice into the 1980's in Europe, and silver nitrate is still used as a topical antimicrobial agent. In the 1960's the very successful burn treatment silver complex, silver sulfadiazine, shown in formula 1 below, was developed. Commercially known as Silvadene® Cream 1%, this complex has remained one of the most effective treatments for preventing infection of second and third degree burns. Silver sulfadiazine has been shown to have good antimicrobial properties against a number of gram-positive and gram-negative bacteria. It is believed that the slow release of silver at the area of the superficial wound is responsible for the process of healing. Studies on surgically wounded rats have shown the effectiveness of both silver nitrate and silver sulfadiazine to aid in the healing process. By using these common silver antimicrobial agents, inflammation and granulation of wounds were reduced, although the complete mechanism for these phenomena is not understood.

In recent years an increasing interest in the field of biodegradable polymers for their use as drug delivery systems has occurred. The majority of this research has included the biodegradable nanoparticles poly(glycolic acid) (PGA), poly (lactic acid) (PLA), and poly(lactic-co-glycolic acid) (PLGA) because they are approved by the FDA. PGA has been used in biodegradable suture materials since the 1970's.

Recent research has explored the loading of commercially available anticancer drugs, such as Paclitaxel (IUPAC name β-(benzoylamino)-α-hydroxy-6,12b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca(3,4)benz(1,2-b)oxet-9-ylester,(2aR-(2a-α,4-β,4a-β,6-β,9-α(α-R*,β-S*),11-α,12-α,12a-α,2b-α))-benzenepropanoic acid), into PLGA nanoparticles for drug delivery. One of the drawbacks of this drug is its hydrophobicity which leads to a slow absorption of the drug into the body. However, the loading of Paclitaxel into PLGA has lead to increased efficacy. This is due mainly to the increase in hydrophilicity of the prepared nanoparticles.

Another existing drug delivery system used for biomedical application is the polyaminophosphazenes with amino acid ester side chains. This class of compounds ultimately degrades into products that are bio-friendly, including phosphates and ammonia. The two main polyaminophosphazenes that have been used to date are poly(di(ethyl glycinato) phosphazene) (PEGP) and poly(di(ethyl alaninato) phosphazene) (PEAP).

SUMMARY OF THE INVENTION

In general, one aspect of the invention is to provide a compound for treating cancer, the compound comprising a metal complex having predetermined characteristics, and which may be incorporated into a polymeric nanoparticle or other delivery system for delivering the metal complex for action on tumor cells.

Another aspect of the invention is to provide a metal complex for treating cancer wherein the metal complex is a silver (I) salt, a silver(I) macrocyclic metal complex, a silver(I) N-heterocyclic carbene or mixtures thereof.

In yet another aspect of the invention, the silver(I) macrocyclic metal complex is:

wherein each R is independently selected from the group consisting of a proton, an alkyl, an ether, an alcohol, a carboxylic acid, an aryl, an amino acid, a peptide, or null, wherein $X_1$, $X_2$ and $X_3$ are independently either sulfur or nitrogen, and when $X_1$, $X_2$ or $X_3$ is sulfur then R is null, wherein the macrocyclic ligand comprised of carbon, $R_{1-3}$, and $X_{1-3}$, represents L, wherein Y is selected from the group consisting of $NO_3$, OAc, SCN, $BF_4$, OTf, $SO_4$, Cl, Br, and I, or may represent L, and wherein Y represents L, then the counter anion is selected from the group consisting of $NO_3^-$, $OAc^-$, $SCN^-$, $BF_4^-$, $OTf^-$, $SO_4^-$, $Cl^-$, $Br^-$, and $I^-$.

A further aspect of the invention, the silver(I) N-heterocyclic carbene is:

wherein $R_1$ and $R_2$ are selected from the group consisting of a halide, a proton, an alkyl, an ether, an alcohol, a nitro, a cyano, and a carboxylic acid, wherein $R_3$ and $R_4$ are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

In yet a further aspect of the invention, the silver(I) N-heterocyclic carbene is:

wherein $R_1$ and $R_2$ are selected from the group consisting of a halide, a proton, an alkyl, an ether, an alcohol, a nitro, a cyano, and a carboxylic acid, wherein $R_3$ and $R_4$ are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

In another aspect of the invention, the silver(I) N-heterocyclic carbene is:

wherein $R_{1-4}$ can are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

In yet another aspect of the invention, a method of treating cancerous cells in a mammal includes the steps of:

administering an effective amount of a silver(I) metal salt incorporated into a biodegradable polymeric nanoparticle.

In another aspect of the invention, a method of treating cancerous cells in a mammal includes the steps of:

administering an effective amount of a macrocyclic silver (I) complex, the macrocyclic complex comprising:

wherein each R is independently selected from the group consisting of a proton, an alkyl, an ether, an alcohol, a carboxylic acid, an aryl, an amino acid, a peptide, or null, wherein $X_1$, $X_2$ and $X_3$ are independently either sulfur or nitrogen, and when $X_1$, $X_2$ or $X_3$ is sulfur then R is null, wherein the macrocyclic ligand comprised of carbon, $R_{1-3}$, and $X_{1-3}$, represents L, wherein Y is selected from the group consisting of $NO_3$, OAc, SCN, $BF_4$, OTf, $SO_4$, Cl, Br, and I, or may represent L, and wherein Y represents L, then the counter anion is selected from the group consisting of $NO_3^-$, $OAc^-$, $SCN^-$, $BF_4^-$, $OTf^-$, $SO_4^-$, $Cl^-$, $Br^-$, and $I^-$.

An aspect of the invention, a method of treating cancerous cells in a mammal includes the steps of:

administering an effective amount of a N-heterocyclic silver(I) complex, the N-heterocyclic complex comprising:

wherein $R_1$ and $R_2$ are selected from the group consisting of a halide, a proton, an alkyl, an ether, an alcohol, a nitro, a cyano, and a carboxylic acid, wherein $R_3$ and $R_4$ are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

In another aspect of the invention, a method of treating cancerous cells in a mammal includes the steps of:

administering an effective amount of a N-heterocyclic silver(I) complex, the N-heterocyclic complex comprising:

wherein $R_1$ and $R_2$ are selected from the group consisting of a halide, a proton, an alkyl, an ether, an alcohol, a nitro, a cyano, and a carboxylic acid, wherein $R_3$ and $R_4$ are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

In yet another aspect of the invention, a method of treating cancerous cells in a mammal includes the steps of:

administering an effective amount of a N-heterocyclic silver(I) complex, the N-heterocyclic complex comprising:

wherein $R_{1-4}$ can are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

In another aspect of the invention, a method of treating cancerous cells in a mammal includes the steps of:

administering an effective amount of a N-heterocyclic silver(I) complex, the N-heterocyclic complex comprising:

wherein $R_{1-4}$ can are selected from the group consisting of a proton, an alkyl, an ether, an alcohol, a carboxylic acid, an aryl, an amino acid, and a peptide, and wherein X is selected from the group consisting of $NO_3$, OAc, SCN, $BF_4$, OTf, $SO_4$, Cl, Br, and I.

DETAILED DESCRIPTION OF THE INVENTION

The use of metal compounds, including metal complexes, in conjunction with biodegradable nanoparticles, such as for use in the treatment of cancer, is set forth as an example of the invention. Other delivery systems are contemplated or may be developed. In an example, the present invention comprises, but is not limited to silver(I) metal complexes as simple salts, silver(I) macrocyclic metal complexes, and silver(I) N-heterocyclic carbenes (NHCs) incorporated within biodegradable nanoparticles for the treatment of cancer.

Nanoparticles may generally vary in size from 10 nm to 1000 nm. These sub-micron sized particles possess certain distinct advantages over microparticles. Nanoparticles, including nanospheres, unlike microspheres, can be used to directly target the tissues via systemic circulation or across the mucosal membrane. This targeting is possible as a result of the capacity of these nanoparticles to be endocytosed by individual cells. It has also been observed that nanoparticles administered intravenously are taken up by cells of mononuclear phagocyte system, mainly in the Kuppfer cells. Such nanoparticles are rapidly cleared from the blood and are usually concentrated in the liver, spleen and blood marrow.

In case of a nanoparticle type delivery system, the therapeutic agent is dissolved, encapsulated, entrapped or chemically conjugated to the nanoparticle matrix depending on the method of fabrication of the device. Typically, the drug is physically and uniformly incorporated and dispersed within a nanosphere matrix. The drug formulated in such a polymeric device is released by diffusion through the polymeric matrix, erosion of the polymeric matrix or by a combination of diffusion and polymer erosion mechanisms. In one embodiment of the invention, biodegradable, polymeric nanoparticles including poly(glycolic acid) (PGA), poly(lactic acid) (PLA), and poly(lactic-co-glycolic acid) (PLGA) are used.

Historically, nanoparticles were investigated primarily for the delivery of simple drug molecules. However, in recent years nanoparticles have attracted considerable attention as potential drug delivery devices in view of their applications in the controlled release of drugs, as carriers of DNA in gene therapy, their ability to target particular organs and tissues and in their ability to encapsulate and delivery peptides, proteins and genes through a peroral route of administration.

Conventionally, the methods used to prepare nanoparticles can be broadly classified into two: (1) dispersion of the preformed polymers, and (2) polymerization of monomers, however; several different variations of each of the above methods have been attempted to optimize the product formulation. Some of the more common variations of the first method that have been used to prepare nanoparticles include (a) solvent evaporation method, (b) spontaneous emulsification/solvent diffusion method and salting out/emulsification-diffusion method. A common theme observed in these cases is an attempt to remove the organic solvent in a controlled manner thereby bringing about the precipitation of the polymeric particles. The encapsulation of the drug is carried out by dissolving the drug in the organic phase containing the polymer or an inner aqueous phase depending on the relative hydrophilicity and solubility of the drug. In case of polymeric nanoparticles prepared by polymerization of monomers, the polymer usually has a lower solubility in the polymerization medium compared to the monomer. This results in the precipitation of the polymer with an increase in the molecular weight of the polymer. A control over the particle size is achieved by altering parameters such as rate of mechanical stirring, type and concentration of surfactant and/or stabilizer used, pH of the polymerization medium, etc. The drug can be encapsulated within the nanoparticles either during the polymerization process or post-polymerization.

One group of nanoparticles includes polyphosphazenes $[PR_2N]_n$. Polyphosphazenes are versatile polymers because they can be functionalized with a large variety of R groups by simply displacing the chlorides of the parent $[PCl_2N]_n$ polymer. The water sensitivity of the polyphosphazene can be varied from water-stable to water-sensitive by the choice of the substituent. In general, most R groups that are bound to the phosphazene backbone via a P—N bond are water sensitive and those that are bound via a P—O bond are water stable. Exceptions to the latter general rule are phosphazenes with glucosyl and glycolic and lactic acid esters substituents that are water-sensitive, even though these substituents are bound via a P—O bond. When $[PR_2N]_n$ polymers react with water, $NH_3$, $H_3PO_4$ (or phosphates) and R—H are formed. Because $NH_3$ and $H_3PO_4$ and biologically compatible, the properties of R—H determines whether water-erodible $[PR_2N]_n$ polymers are biocompatible. Therefore, polyphosphazenes with glucosyl and glycolic and lactic acid esters substituents are biocompatible. Other biologically compatible substituents that give water-erodible phosphazenes include imidazolyl, glyceryl, and esters of amino acids, depsipeptides. With the various biocompatible R groups, hydrolysis of $[PR_2N]_n$ takes days to several months. The water sensitivity can be tailored by synthesizing a polyphosphazene with two, or even three different substituents (of general form $[PR_2N]_x[PRR'N]_y$, $[PR'_2N]_z$) and varying the relative amounts of the two substituents (x, y, and z). Polyphosphazenes have other potentially useful properties. They can be made into nanofibers and, depending on the R substituent, some have cell-adhesion properties.

In this example of the invention, the compounds useful for the treatment of cancer include silver(I) salts that are incorporated within the biodegradable nanomeric polymers including PLA, PGA, and PLGA are generally represented by formula 1 or by formula 2:

1

2 wherein X is represented by $NO_3$, OAc, SCN, $BF_4$, OTf, or $SO_4$ and wherein Y is represented by Li, Na, or K and X is represented by Cl, Br, or I.

The macrocyclic ligands that will be used to chelate to the silver salts represented by formula 1 are represented but not limited to formulas 3-6:

3

4

5

6 wherein each R can vary independently and can be a hydrogen atom, an alkyl such as but not limited to a methyl, an ether such as but not limited to methyl ethyl ether, an alcohol such as but not limited to ethanol, a carboxylic acid such as but not limited to acetic acid, an aryl such as but not limited to benzene, an amino acid such as but not limited to serine or threonine, or a peptide such as but not limited to luetinizing hormone. These R groups can be modified in order to increase the overall solubility of the complexes.

The N-heterocyclic carbenes that will be used to bind to Ag(I) are represented by but not limited to formulas 7-8:

7 wherein $R_{1-2}$ can be independently or non-independently represented by a halide, a proton, an alkyl, an ether, an alcohol, a nitro, a cyano, or a carboxylic acid, wherein $R_{3-4}$ can be independently or non-independently represented by a hydrogen atom, an alkyl such as but not limited to a methyl, an ether such as but not limited to methyl ethyl ether, an alcohol such as but not limited to ethanol, a carboxylic acid such as but not limited to acetic acid, an aryl such as but not limited to benzene, an amino acid such as but not limited to serine or threonine, or a peptide such as but not limited to luetinizing hormone, and wherein X can be represented by $NO_3$, OAc, SCN, $BF_4$, OTf, $SO_4$, $PF_6$, $BPh_4$, Cl, Br, and I. These R groups can be modified for solubility purposes:

8 wherein $R_{1-4}$ can vary independently and can be a hydrogen atom, an alkyl such as but not limited to a methyl, an ether such as but not limited to methyl ethyl ether, an alcohol such as but not limited to ethanol, a carboxylic acid such as but not limited to acetic acid, an aryl such as but not limited to benzene, an amino acid such as but not limited to serine or threonine, or a peptide such as but not limited to luetinizing hormone, and wherein X can be represented by $NO_3$, OAc, SCN, $BF_4$, OTf, $SO_4$, $PF_6$, $BPh_4$, Cl, Br, and I. These R groups can be modified for solubility purposes.

Since preparations of the nanoparticles involves the use of large amounts of water combined with a small amount of an organic solvent, it is understood that the silver(I) metal complexes incorporated within the nanoparticles will form in the organic portion of the mixture in the case of some nanoparticles and in the hydrophobic core of the nanoparticles in the case of other nanoparticles. Therefore, the selected silver(I) metal complexes will need to be hydrophobic. With this understanding, the silver(I) N-heterocyclic carbenes, as shown in formulas 9-13, have been prepared having hydrophobic substituent groups. The silver(I) N-heterocyclic carbenes, as shown in formulas 14 and 15, are further examples wherein $R_1$-$R_4$ represent the same or different hydrophobic alkyl and aryl substituent groups. Formulas 16-21 are further examples of hydrophobic silver(I) N-heterocyclic carbenes.

9

10

11

12

13

14

15

16

17

18

19

20

21

22

In one example, a silver(I) complex as represented in formula 23 has been tested for preliminary anticancer activity against the ovarian cancer cell line NuTu-19. Silver complex 23 was chosen because of its overall stability. This silver(I)-NHC has shown anticancer activity when tested for a period of 72 hours.

23

Figure 1:
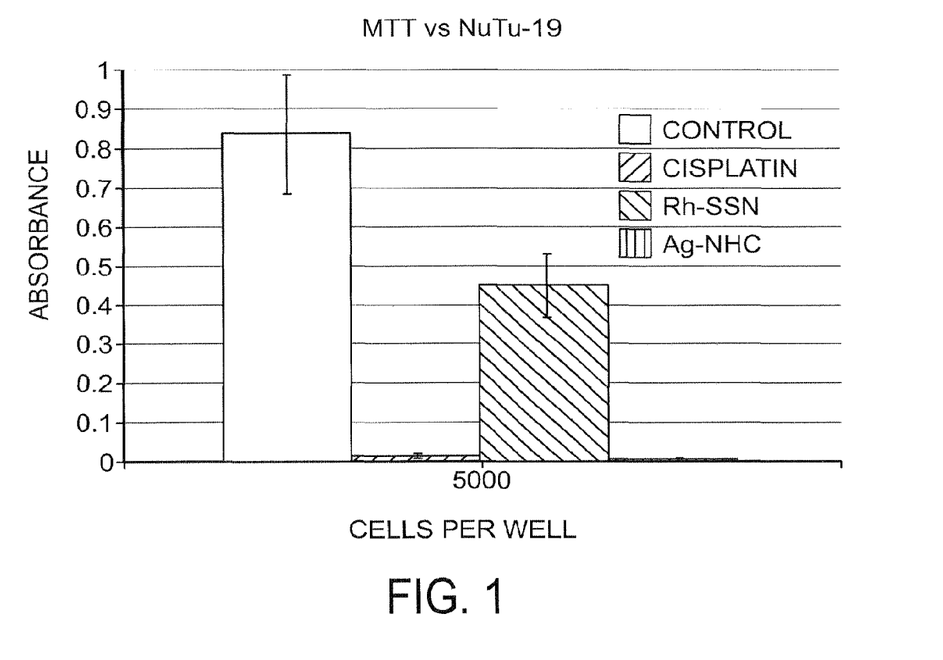
FIG. 1 shows a graph of the activity of compounds in the treatment of the ovarian cancer cell line NuTu-19.

As seen in FIG. 1, the MTT data obtained when testing formula 23 against the ovarian cancer cell line NuTu-19 is shown. In particular, the anticancer activity of formula 23 was compared to cisplatin and a previously patented thiaether-$RhCl_3$ complex that was determined to possess anticancer activity.

Cells were plated at 5000 cells per well in a 96-well plate. All tests were run in triplicate. Cells were allowed to incubate overnight after plating followed by the addition of a 50 µM solution of 23, cisplatin, and thiaether-$RhCl_3$ dissolved in complete cell media. The cells were then incubated for 72 h followed by the addition of MTT dissolved in phosphate buffered saline (PBS) and incubated for another 4 h. A sodium dodecyl sulfate: 0.01M HCl (SDS) solution was then added and the cells were incubated overnight. The SDS solution is added to solubilize the blue formazan crystals that are formed by the reduction of MTT by living cells. The absorbance is then read on a microplate reader. Therefore, the higher the absorbance the more living cells present in cell colony. The graph in FIG. 1 shows that after 72 h of incubation, formula 23, kills all cells at 50 µM.

Figure 2:
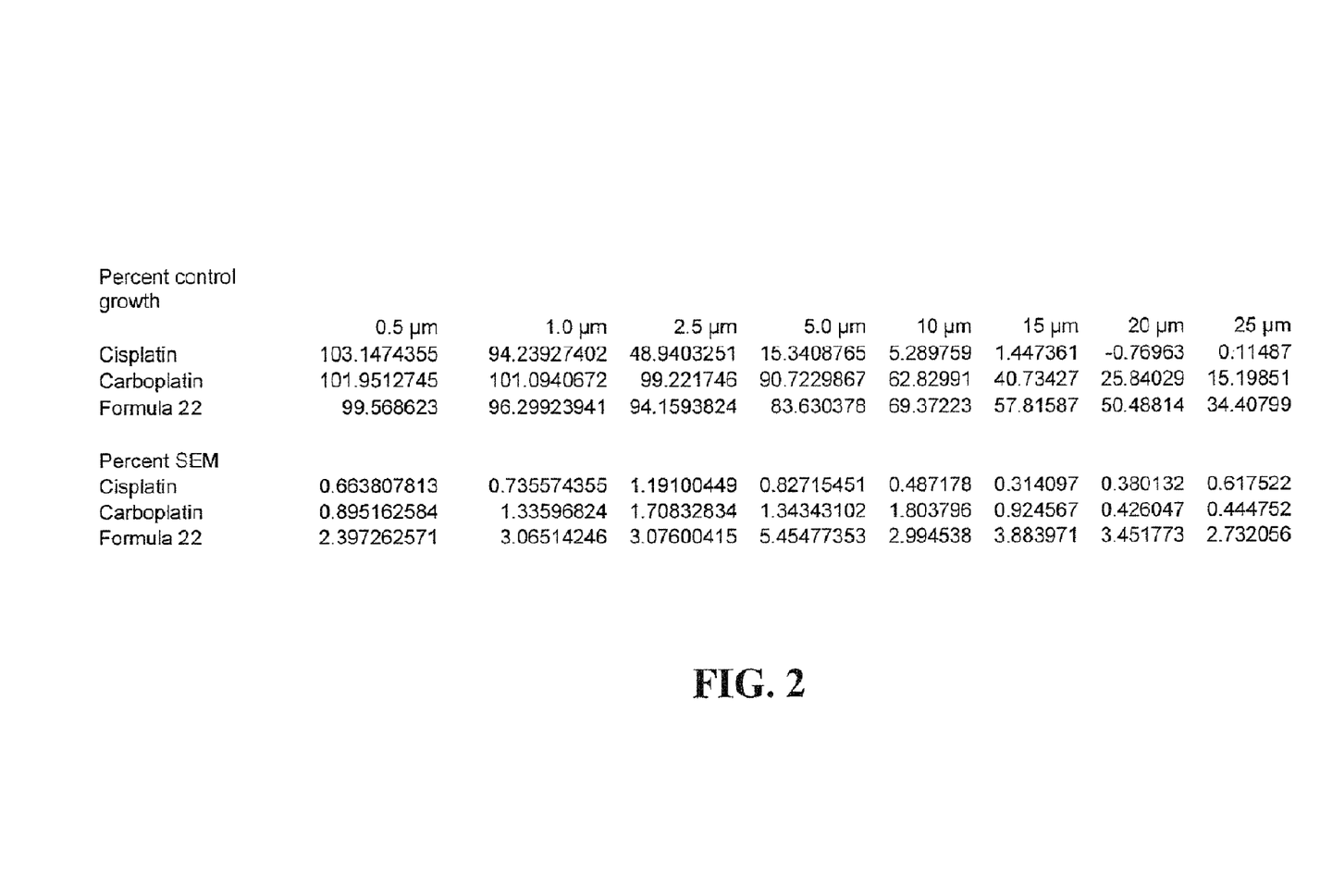
FIG. 2 shows a chart comparing anti-proliferative effects of formula 23, cisplatin and carboplatin on A375 melanoma.
Figure 3:
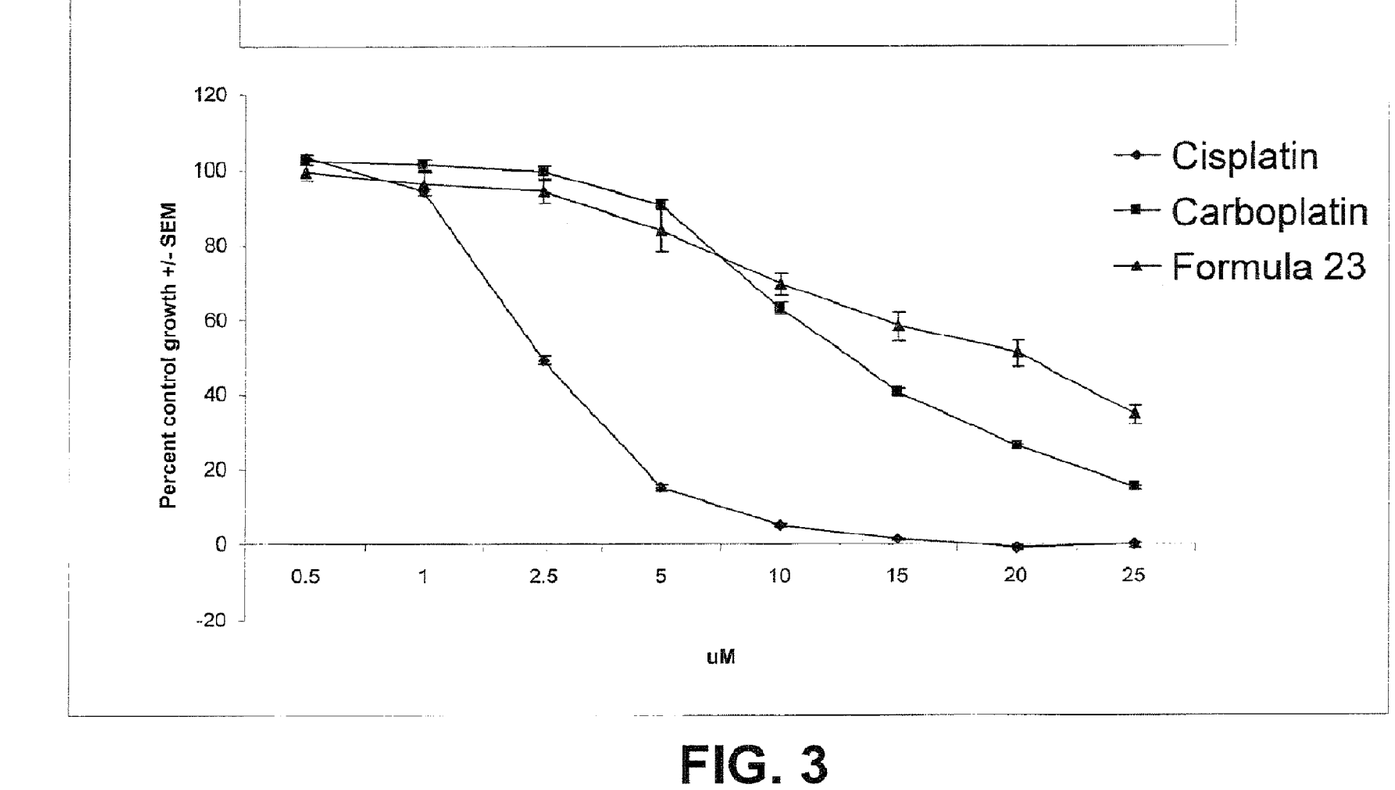
FIG. 3 shows a graph measuring the percent control growth of formula 23, cisplatin and carboplatin on A375 melanoma at various concentrations.

Further studies were conducted with formula 23 against known, commercially available chemotherapy drugs including cisplatin and carboplatin as seen in FIGS. 2-7. The antiproliferative effects of formula 23, cisplatin and carboplatin were investigated on A375 melanoma at 96 hours of growth and are shown in FIGS. 2 and 3. Percent control growth and percent standard error of the means (SEM) were conducted at various concentrations including 0.5 µm, 1.0 µm, 2.5 µm, 5.0 µm, 10 µm, 15 µm, 20 µm and 25 p.m. With regards to percent control growth, it can be seen that formula 23 showed the best control growth when compared to cisplatin and carboplatin for the A375 melanoma.

Figure 4:
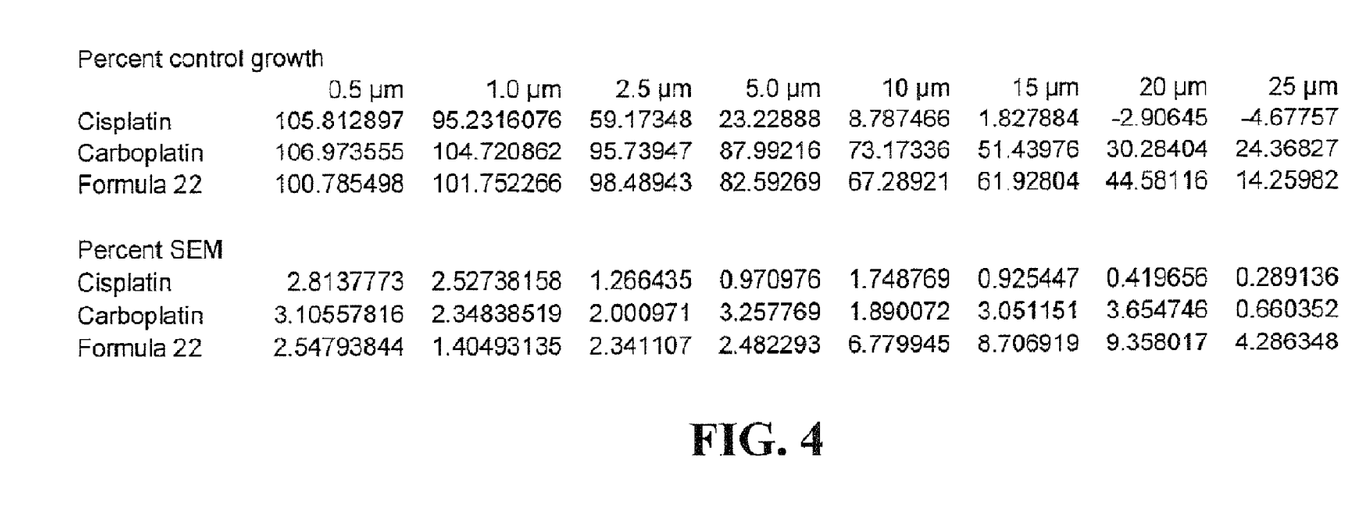
FIG. 4 shows a chart comparing anti-proliferative effects of formula 23, cisplatin and carboplatin on ACHN renal carcinoma.
Figure 5:
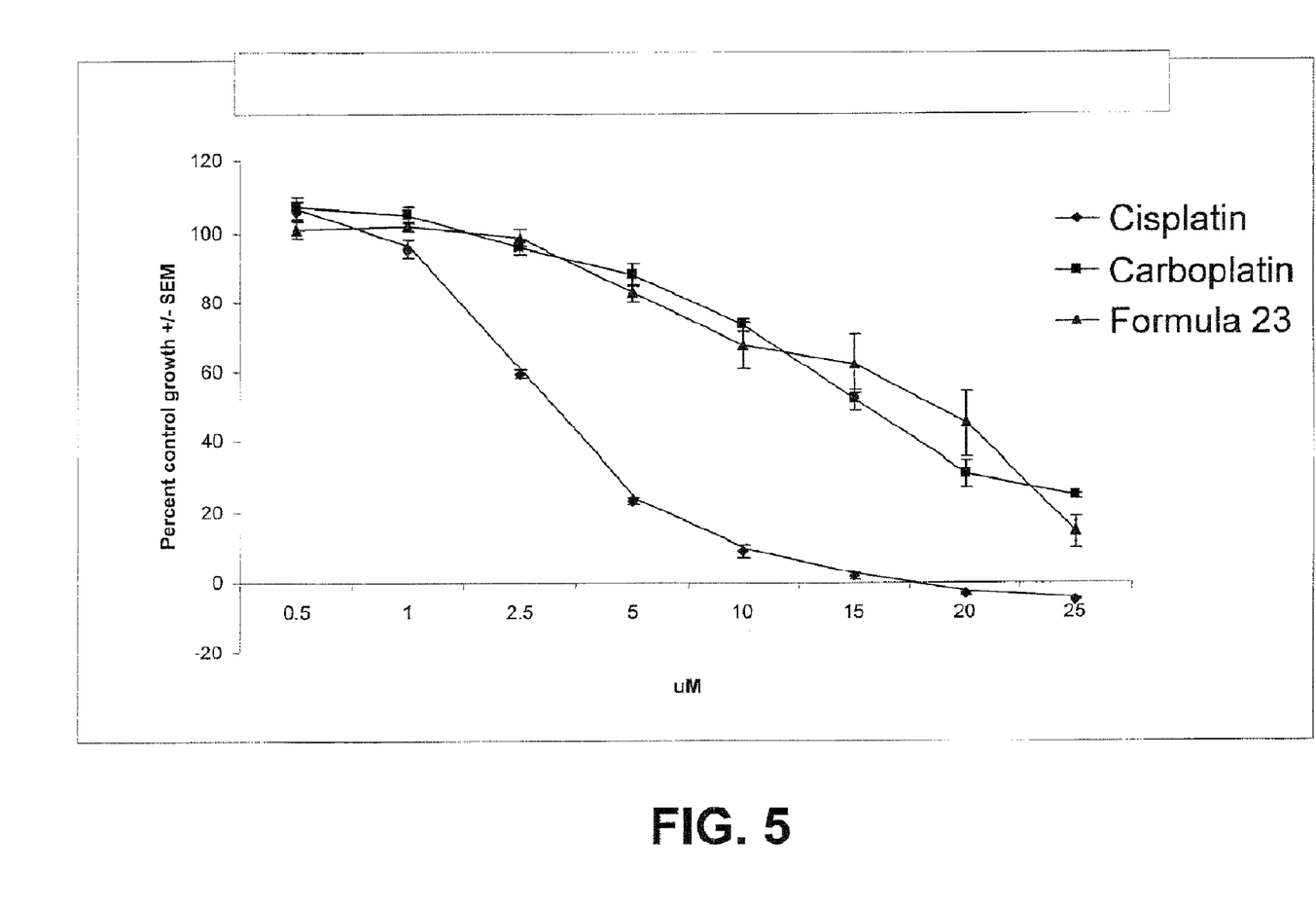
FIG. 5 shows a graph measuring the percent control growth of formula 23, cisplatin and carboplatin on ACHN renal carcinoma at various concentrations.

The anti-proliferative effects of formula 23, cisplatin and carboplatin were investigated on ACHN renal carcinoma at 96 hours of growth and are shown in FIGS. 4 and 5. Percent control growth and percent standard error of the means (SEM) were conducted at various concentrations including 0.5 µm, 1.0 µm, 2.5 µm, 5.0 µm, 10 µm, 15 µm, 20 µm and 25 µm. With regards to percent control growth, it can be seen that formula 23 showed comparable control growth when compared to carboplatin for the A375 melanoma and better control growth when compared to cisplatin for the A375 melanoma.

Figure 6:
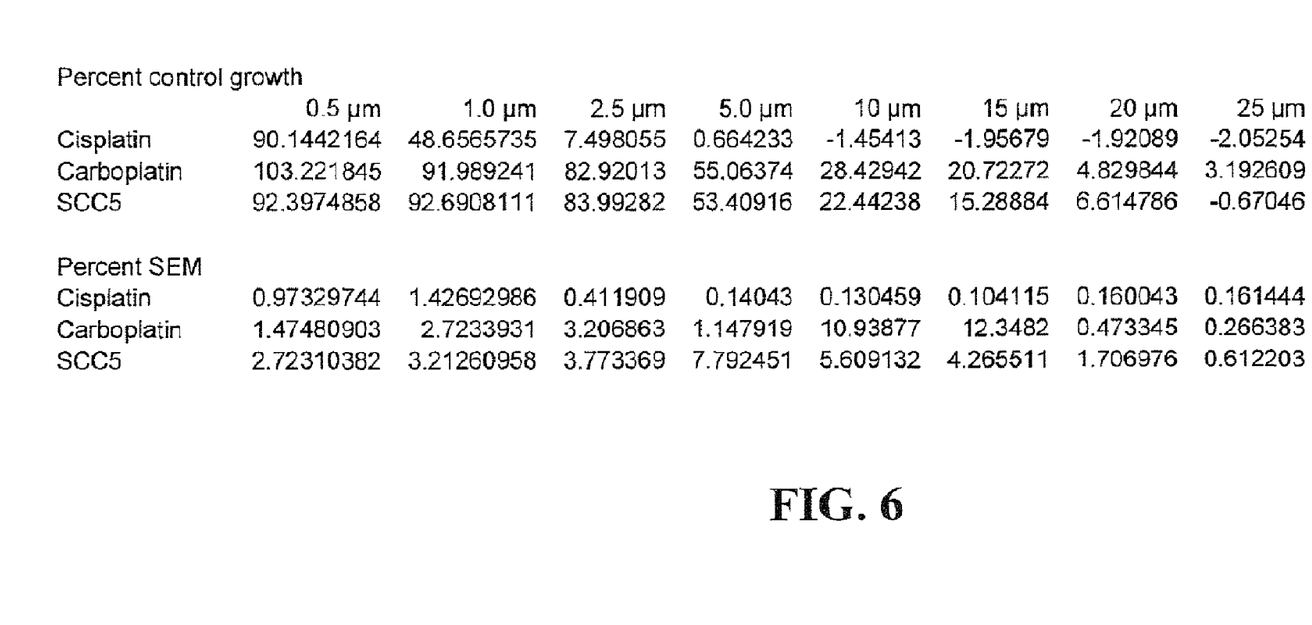
FIG. 6 shows a chart comparing anti-proliferative effects of formula 23, cisplatin and carboplatin on HT1376 colon carcinoma.
Figure 7:
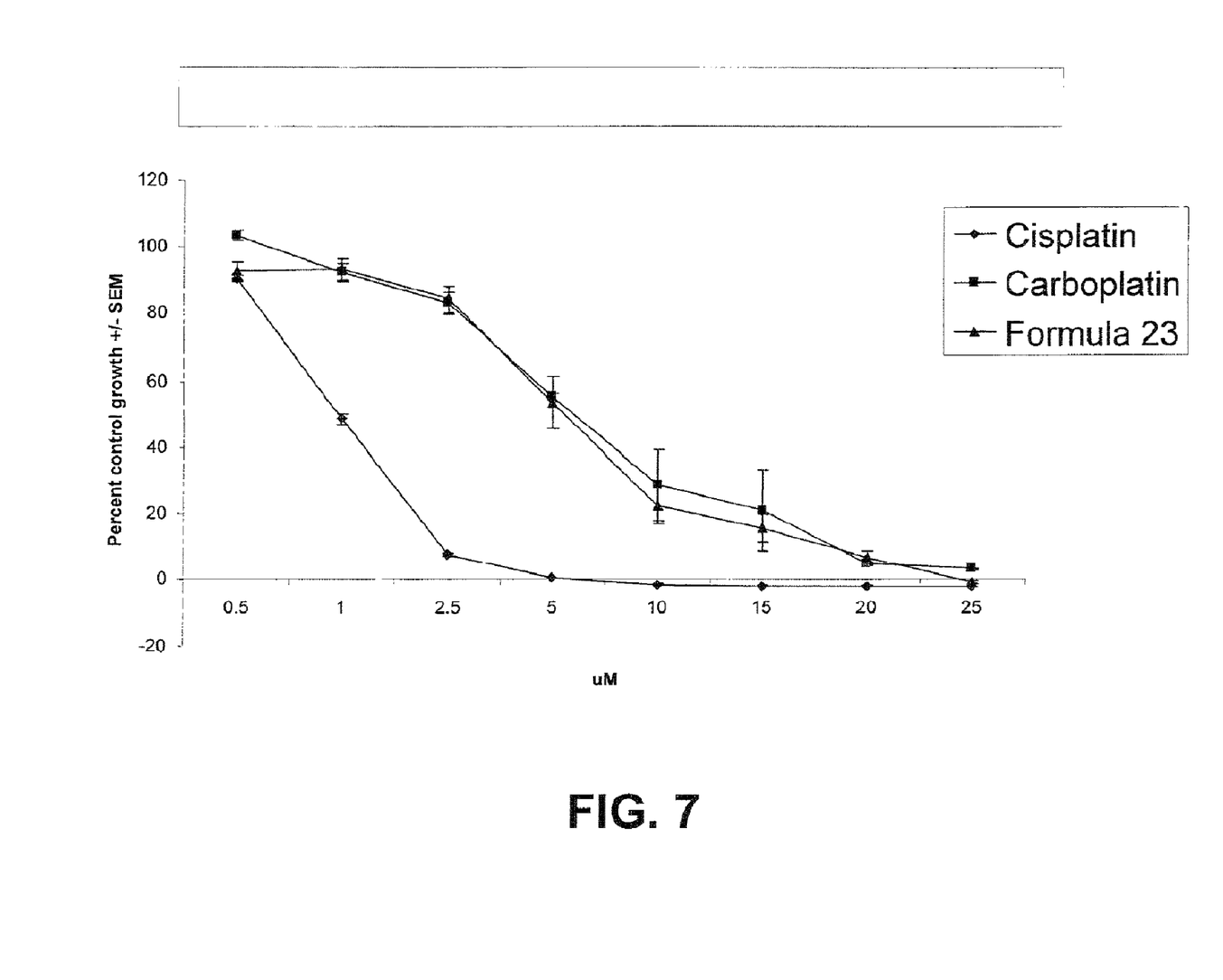
FIG. 7 shows a graph measuring the percent control growth of formula 23, cisplatin and carboplatin on HT1376 colon carcinoma at various concentrations.

The anti-proliferative effects of formula 23, cisplatin and carboplatin were investigated on HT1376 colon carcinoma at 96 hours of growth and are shown in FIGS. 6 and 7. Percent control growth and percent standard error of the means (SEM) were conducted at various concentrations including 0.5 µm, 1.0 µm, 2.5 µm, 5.0 µm, 10 µm, 15 µm, 20 µm and 25 µm. With regards to percent control growth, it can be seen that formula 23 showed comparable control growth when compared to carboplatin and cisplatin for the HT1376 colon carcinoma.

The term effective amount defines the dosage needed for proper treatment. The dosage will vary based on the silver(I) metal complex used and the physiological characteristics of the patient, and the nature and location of the cancer cells being treated. The type of drug administration will also vary depending on the nature and location of the cancer cells being treated, or other characteristics.

Further silver(I) metal complexes were prepared from 4,5-dihydroimidazole derivatives as seen in formulas 24-27.

The functional groups, R, as seen in formula 27 serve to alter solubility properties of the complexes. In one embodiment, the R group is an alcohol. Suitable alcohols include ethanol and propanol. For formula 26, n has a value between 1 and 200. Formulas 24-27 were found to almost immediately decompose in water at ambient temperature in light. It was also observed that formulas 24-27 exhibited poor stability in a physiological amount of sodium chloride. Decomposition of formulas 23-26 resulted in an active silver and imidazolium cation. Formulas 24 and 26 were shown to produce severe toxicity in rat models via IV tail injection.

The method of treatment can be but is not limited to intravenous injection, intraperitoneal injection, inhalation, or oral ingestion. If the injection method is used, the drug can be dissolved in a suitable solvent. The choice solvent is typically a physiological saline solution. This solution can range from 0.5 to 1.0% sodium chloride in water because at this concentration the saline solution is of biological significance as it is isotonic with blood plasma. Another suitable solvent is dimethyl sulfoxide (DMSO). Other biologically acceptable solvents are also acceptable. The inhalation method will involve nebulization of the drug, as the drug will be inhaled as an aerosol. The oral ingestion method includes ingestion of the drug as a pill, capsule, caplet or tablet.

Formulation of the silver(I) metal complexes as a nanoparticle delivery system confers various clinical advantages. First, the formulation promotes slow leaching of the parent silver(I) metal complexes and active silver cation, thus providing a depot delivery of active drug. This slow-release effect allows for increased dosing intervals and increased patient compliance. Furthermore, these particles can be taken up by alveolar macrophages and delivered to the systemic circulation. Previous studies have shown that aggregate particles in the size range of 1-5 μm can be phagocytized by macrophages, which subsequently migrate from the lung surface to the lymphatic system. Since the lymphatic system is intimately connected to the immune system as a whole, targeting of the silver(I) metal complexes drugs to the macrophages may offer benefits over traditional systemic delivery. If the immune system is targeted in this way, dose reduction is possible, yielding the same clinical outcomes as higher dosed oral or systemic type antimicrobials and eliminating potential dose-related side effects.

In one example, the silver(I) metal complexes of the present invention can be used to recognize tumor-associated antigens and tumor specific antigens to deliver a therapeutic and cytotoxic agent to cancerous tissue and cells, while minimizing exposure of the cytotoxic agents to non-cancerous, healthy tissue and cells. Antibodies such as, for example, monoclonal antibodies that recognize tumor associated antigen or tumor specific antigen, are complexed with, for example, streptavidin and introduced into a patient. The antibody recognizes the tumor associated antigen and associates with is, thereby localizing the streptavidin in the tumor tissue. Subsequently, the silver(I) metal complexes, which have biotin bound thereto, are introduced into the patient. The streptavidin binds the biotin and localizes the silver(I) metal complexes at the tumor tissue.

Based upon the foregoing disclosure, it should now be apparent that the use of metal compounds, including silver metal complexes, in conjunction with biodegradable nanoparticles for the treatment of cancer as described herein will carry out the objects set forth hereinabove. It is, therefore, to be understood that any variations evident fall within the scope of the claimed invention and thus, the selection of specific component elements can be determined without departing from the spirit of the invention herein disclosed and described.

What is claimed is:

1. A compound for treating cancer, the compound comprising:
   a silver (I) metal complex incorporated into a biodegradable polymeric nanoparticle, wherein the silver (I) metal complex comprises wherein R1 and R2 are selected from the group consisting of a halide, a proton, an alkyl, an ether, an alcohol, a nitro, a cyano, and a carboxylic acid, and wherein R3 and R4 are selected from the group consisting of a proton, an alkyl, an ether, an alcohol, a carboxylic acid, an aryl, an amino acid, and a peptide.

2. The compound of claim 1, wherein the biodegradable polymeric nanoparticle is selected from the group consisting of poly(glycolic acid), poly(lactic acid), and poly(lactic-co-glycolic acid).

3. A method of treating cancerous cells in a mammal, the method comprising the steps of: administering an effective amount of a N-heterocyclic silver(I) complex, the N-heterocyclic complex comprising:

wherein R1 and R2 are selected from the group consisting of a halide, a proton, an alkyl, an ether, an alcohol, a nitro, a cyano, and a carboxylic acid, and wherein R3 and R4 are selected from the group consisting of a proton, an alkyl, an ether, an alcohol, a carboxylic acid, an aryl, an amino acid, and a peptide.

4. The method of claim 3, wherein the N-heterocyclic silver(I) complex is incorporated into a biodegradable polymeric nanoparticle.

5. The method of claim 4, wherein the biodegradable polymeric nanoparticle is selected from the group consisting of poly(glycolic acid), poly(lactic acid), and poly(lactic-co-glycolic acid).

* * * * *

UNITED STATES PATENT AND TRADEMARK OFFICE
Certificate

Patent No. 8,282,944 B2　　　　　　　　　　　　　　　　　　　　Patented: October 9, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Wiley J. Youngs, Akron, OH (US); Khadijah Hindi, Akron, OH (US); Doug Medvetz, Elyria, OH (US); and Matthew J. Panzner, Akron, OH (US).

Signed and Sealed this Seventh Day of January 2014.

DAVID J. BLANCHARD
Supervisory Patent Examiner
Art Unit 1619
Technology Center 1600